(12) United States Patent
Hill et al.

(10) Patent No.: US 8,277,751 B2
(45) Date of Patent: Oct. 2, 2012

(54) TISSUE PAPER WITH PH-INDICATOR FUNCTION

(75) Inventors: Walter Hill, Hofheim (DE); Sarah Marinoni, Lurago Marinone (IT)

(73) Assignee: SCA Hygiene Products GmbH, Mannheim (DE)

( * ) Notice: Subject to any disclaimer, the term of this patent is extended or adjusted under 35 U.S.C. 154(b) by 531 days.

(21) Appl. No.: 11/917,465

(22) PCT Filed: Jun. 17, 2005

(86) PCT No.: PCT/EP2005/006557
§ 371 (c)(1),
(2), (4) Date: May 9, 2008

(87) PCT Pub. No.: WO2006/133728
PCT Pub. Date: Dec. 21, 2006

(65) Prior Publication Data
US 2010/0215542 A1 Aug. 26, 2010

(51) Int. Cl.
*G01N 21/75* (2006.01)
(52) U.S. Cl. ........ 422/401; 422/420; 422/426; 422/421; 424/405; 424/443; 436/20; 436/66
(58) Field of Classification Search .............. 8/401, 478; 427/207.1, 208, 209; 101/2, 3.1; 422/55, 422/57; 436/163, 805
See application file for complete search history.

(56) References Cited

U.S. PATENT DOCUMENTS

| | | | |
|---|---|---|---|
| 4,681,576 A | | 7/1987 | Colon et al. |
| 5,071,623 A | * | 12/1991 | Akutsu ........................... 422/56 |
| 5,143,023 A | * | 9/1992 | Kuhns ........................... 119/173 |
| 5,753,331 A | * | 5/1998 | Jeffrey ............................. 428/43 |
| 5,830,765 A | * | 11/1998 | Santioemmo et al. .......... 436/66 |
| 6,495,368 B1 | * | 12/2002 | Wallach ........................... 436/20 |
| 2003/0206940 A1 | * | 11/2003 | Gott et al. ..................... 424/443 |
| 2004/0191118 A1 | * | 9/2004 | Mody ............................ 422/56 |
| 2006/0222675 A1 | * | 10/2006 | Sabnis et al. .................. 424/405 |
| 2007/0017042 A1 | * | 1/2007 | Cincotta et al. ................... 8/643 |

FOREIGN PATENT DOCUMENTS

| | | |
|---|---|---|
| GB | 1018563 A | 1/1966 |
| JP | 2855292 B2 * | 2/1999 |
| WO | WO9617245 A | 6/1996 |

OTHER PUBLICATIONS

Mar. 14, 2006 International Search Report in corresponding PCT/EP2005/006557.

* cited by examiner

*Primary Examiner* — Sally Merkling
(74) *Attorney, Agent, or Firm* — Young & Thompson

(57) ABSTRACT

The present invention relates to a tissue paper with pH-indicator function, specifically a toilet paper that can be used to diagnose abnormal pH changes of the human urine as accompanying for instance acetonemic vomiting or diabetes.

9 Claims, No Drawings

TISSUE PAPER WITH PH-INDICATOR FUNCTION

The present invention relates to a tissue paper with pH-indicator function, specifically a toilet paper that can be used to diagnose abnormal pH changes of the human urine as accompanying for instance acetonemic vomiting or diabetes.

1 BACKGROUND ART

Acetonemic vomiting occurs primarily with psychologically and vegetatively labile infants and is often prompted by wrong diet, food allergy, an infestation with worms or infections. After an initial headache accompanied with lack of appetite and nausea, the body starts to excrete acetone into the breathing air and urine. Simultaneously, the infant suffers from vigorous, often uncontrollable vomiting, apathy, heavy breathing and exsiccosis. Characteristic for this disease is a metabolic acidosis accompanying the increase of acetone which is caused by overproduction and insufficient consumption of acetyl-CoA. There is even the risk that the child falls in a so-called ketonemic coma.

Acetonemic vomiting is currently diagnosed by regular pH-measurements of the child's urine. The procedure employed is relatively cumbersome and is felt to be a burden by both the parents using it and the children suffering from the disease. The child has to collect its urine in a container. Then, an indicator strip is dipped into the container to evaluate the pH value (acidity level) of the urine. Often, it is only the outer tip of this strip, into which the pH indicator is incorporated, which makes it more difficult to determine potential colour changes correctly and precisely.

Moreover, there are other diseases like diabetes where the pH of urine can be taken as a signal for the state of the patient and a correctly applied therapy.

U.S. Pat. No. 5,769,813 describes a tampon applicator comprising a pH indicator for testing excreted biological fluids. It is stated that this tampon serves for determining the pH balance of biological fluid excreted from the vaginal cavity to detect the presence of undesired bacterial activity.

EP 1 043 377 A2 discloses a wetness indicating hot melt adhesive and a disposable product including diapers and sanitary napkins containing the same. It is explained that in such disposable products it is desirable to know if the product has become wet with water or urine. The hot melt adhesive comprises as essential components
a) 20 to 80 wt % of sulfonated polyester,
b) 3 to 30 wt % of acidic plasticizer; and
c) 0.05 to 3 wt % of an indicating agent capable of changing colour in response to changes in pH.

A wetness indicating holt melt adhesive is also the subject matter of U.S. Pat. No. 4,681,576. The adhesive contains 20 to 70 wt % of polymer, 35 to 100 wt % of which is water sensitive polymer; 27 to 60 wt % of organic acid and 0 to 30 wt % of water-soluble wax and wetness indicating agent which changes the color of the composition rapidly in response to moisture therein.

Correspondingly, it is one technical object of the present invention to provide a simplified diagnostic tool for detecting and monitoring pH changes in the urine as caused by metabolic and/or physiological disorders, such as acetonemic vomiting or diabetes. Other technical objects will become apparent from the following more detailed description of the invention.

2 BRIEF SUMMARY OF THE PRESENT INVENTION

The above technical objects are solved by a tissue paper comprising a pH indicator substance. The term "tissue paper" includes for example handkerchiefs, toilet papers, facials, kitchen towels or wipes, whereby toilet papers are especially preferred.

The contact of the tissue paper of the invention with just a few drops of child's urine allows the determination of undesired and abnormal pH changes. The present invention thus eliminates a cumbersome testing routine as used in the prior art. According to the present invention, the lacking necessity to collect urine samples makes the entire testing procedure more hygienic. The simplicity of the present invention allows children to conduct the test themselves and may even involve an element of fun, if bright colors appear, which will increase their willingness to subject to this test.

3 DETAILED DESCRIPTION OF THE INVENTION

The toilet paper of the present invention, which comprises a pH indicator substance for detecting undesired and abnormal pH changes in the urine, provides a greatly simplified diagnostic tool for all diseases accompanied with deviations from normal urine pH (5.8 to 7.4 according to EP 1 043 377). Although, in principle, the invention can also be used to detect pH changes towards a more alkaline pH, it is preferably employed for diagnosing and supervising diseases with a concomitant acidosis such as acetonemic vomiting or diabetes.

The tissue paper, especially toilet paper of the invention can be made from known paper types used for this purpose. It is preferably a tissue paper having one or preferably more tissue plies whereof each ply may consist of several layers. In a more preferred embodiment, the tissue paper of the invention consists of 2, 3 or 4 plies which may have a different layering and different compositions.

Tissue paper is defined as a soft absorbent paper having a low basis weight. One generally selects a basis weight of 8 to 40 $g/m^2$, especially 10 to 30 $g/m^2$, preferably 10 to 25 $g/m^2$ per ply. The total basis weight of multiple-ply tissue products is preferably equal to a maximum of 80 $g/m^2$, more preferably to a maximum of 60 $g/m^2$, and most preferably to a maximum of 50 $g/m^2$. Its density is typically below 0.6 $g/cm^3$, preferably below 0.30 $g/cm^3$ and more preferably between 0.08 and 0.20 $g/cm^3$.

The production of tissue is distinguished from paper production by its extremely low basis weight and its much higher tensile energy absorption index (see DIN EN 12625-4 and DIN EN 12625-5). Paper and tissue paper also differ in general with regard to the modulus of elasticity that characterizes the stress-strain properties of these planar products as a material parameter.

A tissue's high tensile energy absorption index results from the outer or inner creping. The former is produced by compression of the paper web adhering to a dry cylinder as a result of the action of a crepe doctor or in the latter instance as a result of a difference in speed between two wires ("fabrics"). This causes the still moist, plastically deformable paper web to be internally broken up by compression and shearing, thereby rendering it more stretchable under load than an uncreped paper.

Moist tissue paper webs are usually dried by the so-called Yankee drying, the through air drying (TAD) and/or the impulse drying method.

The fibers contained in the tissue paper are mainly cellulosic fibres, such as pulp fibers from chemical pulp (e.g. Kraft sulfite and sulfate pulps), mechanical pulp (e.g. ground wood), thermo mechanical pulp, chemo-mechanical pulp and/or chemo-thermo mechanical pulp (CTMP). Pulps derived from both deciduous (hardwood) and coniferous (softwood) can be used. The fibers may also be or include recycled fibers, which may contain any or all of the above categories. The fibers can be treated with additives—such as fillers, softeners, such as quaternary ammonium compounds and binders, such as conventional dry-strength agents or wet-strength agents used to facilitate the original paper making or to adjust the properties thereof. The tissue paper may also contain non-pulp types of fibers, e.g. regenerated cellulosic fibres or synthetic fibers enhancing, for instance, strength, absorption, smoothness or softness of the paper.

Tissue paper may be converted to the final tissue product in many ways, for example, by embossing or laminating it into a multi-ply product, rolled or folded.

The tissue manufacture process essentially comprises
a forming that includes the headbox and the wire portion,
b the drying portion (TAD (through air drying)) or conventional drying on the yankee cylinder) that also usually includes the crepe process essential for tissues,
c typically the monitoring and winding area.

A wet fibrous web can be formed in step (a) by placing the fibers, in an oriented or random manner, on one or between two continuously revolving wires of a paper making machine while simultaneously removing the main quantity of water of dilution until dry-solids contents of usually between 12 and 35% are obtained.

Drying the formed primary fibrous web occurs in one or more steps by mechanical and thermal means until a final dry-solids content of usually about 93 to 97%. In the case of tissue making, this stage is followed by the crepe process which crucially influences the properties of the finished tissue product in conventional processes. The conventional dry crepe process involves creping on a usually 4.5 to 6 m diameter drying cylinder, the so-called yankee cylinder, by means of a crepe doctor with the aforementioned final dry-solids content of the raw tissue paper (wet creping can be used if lower demands are made of the tissue quality). The creped, finally dry raw tissue paper (raw tissue) is then available for further processing into the paper product or tissue paper product according to the invention.

In addition to the conventional tissue making process described above, the tissue papers according to the invention may also be produced using a modified technique in which an improvement in specific volume is achieved by a special kind of drying within process section b and in this way an improvement in the bulk softness of the thus made tissue paper is achieved. This process, which exists in a variety of subtypes, is termed the TAD (through air drying) technique. It is characterized by the fact that the "primary" fibrous web (like a nonwoven) that leaves the sheet making stage is pre-dried to a dry-solids content of about 80% before final contact drying on the yankee cylinder by blowing hot air through the fibrous web. The fibrous web is supported by an air-permeable wire or belt and during its transport is guided over the surface of an air-permeable rotating cylinder drum. Structuring the supporting wire or belt makes it possible to produce any pattern of compressed zones broken up by deformation in the moist state, resulting in increased mean specific volumes and consequently leading to an increase in bulk softness without decisively decreasing the strength of the fibrous web.

Another possible influence on the softness and strength of the raw tissue lies in the production of a layering in which the primary fibrous web to be formed is built up by a specially constructed headbox in the form of physically different layers of fibrous material, these layers being jointly supplied as a pulp strand to the sheet making stage.

When processing the raw fibrous web or raw tissue paper into the final product (converting section), the following procedural steps are normally used individually or in combination: cutting to size (longitudinally and/or cross cutting), producing a plurality of plies, producing mechanical ply adhesion, volumetric and structural embossing, ply adhesion, folding, imprinting, perforating, application of lotions, smoothing, stacking, rolling up and packaging.

To produce multi-ply tissue paper an intermediate step preferably occurs with so-called doubling in which the raw tissue in the finished product's desired number of plies is usually gathered on a common multiply master roll.

The processing step from the raw tissue that has already been optionally wound up in several plies to the finished tissue product occurs in processing machines which include operations such as repeated smoothing of the tissue, edge embossing, to an extent combined with full area and/or local application of adhesive to produce ply adhesion of the individual plies (raw tissue) to be combined together, as well as longitudinal cut, folding, cross cut, placement and bringing together a plurality of individual tissues and their packaging as well as bringing them together to form larger surrounding packaging or bundles. The individual paper ply webs can also be pre-embossed and then combined in a roll gap according to the foot-to-foot or nested methods.

According to the invention, any suitable pH indicator substance is included in tissue paper, preferably toilet paper, as described above. Depending on the type of tissue paper, vehicle (aqueous solution, lotion, printing color, adhesive, etc. as explained below) and disease to be diagnosed, the pH indicator substance is selected from compounds which show a color change in the pH range to be observed and have excellent skin compatibility. The term "color change" includes a change of color tones (e.g. blue to red), a change from colorless to colored, and vice versa. Examples for suitable pH indicator substances are commercially available and involve Ethyl Red, Bromophenol Blue, Bromocresol Green, 1-Napthyl Red, Bromcresol Green sodium salt, 2,5-Dinitrophenol, 4-Nitrophenol, or Bromoxylenol Blue. Preferred pH indicator substances change color in a pH range of from 3.5 to 5.7, especially 4.0 to 5.7 to and are preferably colorless or have a pale color in the pH range of normal urine (5.8 to 7.4). Preferred embodiments of these pH indicator substances comprise litmus (red at pH 4.5 and blue at pH 8.3), Alizarin (Red)S (yellow at pH 4.3 and pink at pH 6.3), Methyl Red (red at pH 4.4 and orange at pH 6.2) including its sodium salt, Bromphenol Red (yellow at pH 4.7 and purple at pH 6.3), Chlorophenol Red (yellow at pH 4.8 and purple at pH 6.4) Hematoxylin (yellow at pH 5.0 and violet at pH 7.2) and Bromocresol Purple (yellow at pH 5.2 and purple at pH 6.8).

The amount of the pH indicator substance preferably ranges from $10^{-5}$ weight-% to $10^{-1}$ weight-%, in particular $5 \times 10^{-5}$ weight-%. to $5 \times 10^{-2}$ weight-%, based on the dry tissue paper (prior to any converting treatment).

There are various techniques for incorporating the pH indicator substance in the tissue paper of the invention.

For instance, it is conceivable, but not necessarily preferred to treat the papermaking furnish prior to the headbox with a pH indicator substance having the capacity to strongly bind to the typically anionic charges occurring on pulp fibers thereby minimizing the loss of material.

Moreover, after formation the still moist fibrous web may be treated with an aqueous solution of the pH indicator substance, for instance by spraying or by coating the solution on the web.

One further alternative lies in treating the already dried and creped web shortly after the drying (Yankee) cylinder, but still within the paper machine with an aqueous solution of the pH indicator substance, for instance prior to, intermediate of or after calendaring steps.

Generally, it is however preferred to incorporate the pH indicator substance into the tissue paper outside the paper machine, preferably as one step of the aforementioned converting operations. Correspondingly, it is desirable to subject dry and creped tissue paper, be it single- or multi-ply, to the corresponding treatment with a pH indicator substance or a vehicle for it.

According to one embodiment, the tissue paper is treated with a lotion comprising the pH indicator substance. Preferably, the lotion is of oil-in-water (O/W) type wherein the outer aqueous phase has a slightly acidic or neutral pH as normal urine and includes at least one suitable pH indicator substance. One suitable example for such a lotion is described in EP 1 225 277 A and comprises
A) at least one oil,
B) an (O/W) emulsifier or (O/W) emulsifier combination, and
C) 6 to 35 wt % of water, based on the total weight of the lotion composition.

This lotion only needs to be adapted with respect to the necessary presence of a pH indicator substance in the aqueous phase and a possible adjustment of the pH value. The lotion containing the pH indicator substance is preferably applied to one or both outer sides of a single- or multi-ply tissue paper in line with techniques known in the art, such as spraying or printing.

According to one further embodiment, a suitable pH indicator substance is preferably printed on one or both outer sides of the tissue paper in a known fashion and in a regular or irregular pattern. This can be achieved by the following printing techniques: flexo printing, gravure printing, offset printing, ink jet printing, screen printing or by any other printing technique known in the art.

In addition to this, the pH indicator can be applied on the tissue paper by any usual application technique known in the art, for example by spraying or coating.

Generally, aqueous or organic solutions or dispersions of the pH indicator substance are employed for this purpose followed by evaporating the solvent (water or organic) after printing. It is however also possible to formulate a type of solid ink by admixing the pH indicator substance with suitable solid vehicles such as polymeric binders or wax. The resulting solid ink is melted prior to or during the printing step on the tissue paper and subsequently solidified thereon.

According to one preferred embodiment, one or both outer sides of the tissue paper are provided with a barrier layer before a pH indicator substance is printed thereon. It is more preferred that the barrier layer substance is printed in register with the pattern of the pH-indicator substance. The term "in register" means that the two pattern of pH-indicator substance and barrier substance, respectively, preferably coincide in shape, size and distribution. This includes the possibility that the lines constituting the barrier layer pattern are somewhat wider (preferably by 0.5 to 2 mm) than the corresponding lines of the pH indicator substance pattern, for instance 1 mm to 3 mm (barrier layer) over 0.5 mm to 2.5 mm (pH indicator substance). Suitable barrier layer substances are those preventing a possible undesired interaction between the paper ply (specifically the pulp fibers and papermaking additives contained therein) and the pH indicator substance that could lead to a premature pH change, etc. Suitable barrier layer substances include, but are not limited to impermeable films made from special polymers, such as polyolefins, polyester or polyamide or waxes such as carnauba wax. Polyolefins can be modified by incorporating monomers carrying polar groups.

This embodiment is preferably manufactured in a method comprising the steps of
  moving the continuous web (to be converted later to tissue paper) in a direction of its longitudinal extension,
  applying a regular or irregular pattern of a barrier layer substance by means of a first roll,
  applying the same regular or irregular pattern of a pH indicator substance or a vehicle containing the same by means of a second roll, and
  concurrently controlling the repetitive surface speed of the continuous web and the phasing between the first roll and the second roll so as to bring the first pattern and the second pattern in a register with respect to each other.

This is preferably achieved by controlling web elongation by an infeed nip and an outfeed nip before and after the step of applying the first pattern and/or the step of applying the second pattern and relaxing the web after it leaves the outfeed nip. Preferably, the speed ratio between the step of applying the first pattern and the step of applying the second pattern and the phasing thereof is controlled by a feedback control of the position of the continuous web relative to a reference point. Such a method is for instance disclosed in U.S. 60/515,431.

According to one further embodiment, the pH indicator substance is not located on the outer side(s) as in the variants explained above, but incorporated into a laminating adhesive. Accordingly, a multi-ply tissue paper is provided wherein at least two plies are glued together by means of an adhesive comprising a pH indicator substance.

The ingredients of the laminating adhesive to be used preferably carry functional groups in a type and number that impart the adhesive a slightly acidic or neutral nature. This will ensure that, upon contact with overly acidic urine from patients suffering from a metabolic disorder, the pH quickly changes to an acidic value (e.g. 3 or 4).

The adhesives employed for chemically produced ply bonding often contain components soluble or dispersible in water such as polyacrylic acid or polymethacrylic acid or their derivatives, polyvinylalcohol, polyvinylacetate, carboxymethylcellulose or starch, polyurethanes or copolymers of styrene and butadiene. To enhance the bonding capacity of the adhesive when wet it is possible to add small amounts of water-soluble cationic polymer (e.g. glyoxalated polyacrylamide, polyethylenimine or polyamidoepichlorohydrin resin in accordance with the teaching of WO 97/11226 or polyvinylamine as described in WO 2001/085441).

Moreover, it is possible to use hot melt adhesives of the following type: polyethylene hot melts, polyvinylacetate, polyurethanes, dextrine/starch-based adhesives, natural rubber latex, casein and polyacrylic adhesives, whereby polyvinylacetate, dextrine/starch-based adhesives and natural rubber latex are preferably used.

There is no specific limitation regarding the laminating technique to be used. To bond a plurality of the plies to each other, the adhesive is applied to at least part of the contact surface of the plies. For the tissue paper of the present invention two strip-shaped glued zones may be provided running parallel to each other and in the vicinity of the two edges of the web. Generally, it is however preferred to apply the adhesive in a design pattern e.g. flowers, animals, etc.) since this contributes, after the necessary pH change, to the optical attractiveness of the resulting product for the consumer, especially children. Furthermore, substantially the complete surface area may be coated with the adhesive, preferably in combination with an embossed pattern extending over the same surface area. With "substantially the complete surface" we mean that there are essentially no macroscopic zones free of adhesive. This includes the possibility that the adhesive is applied in a discontinuous fashion, preferably in a specific regular pattern over the entire surface.

For applying the adhesive the following systems may be used for example:

roll application by means of a dip roll and transfer roll, roll application by means of a screen roll, which has a knife, and a transfer roll or an application roll, spray application directly to the product or indirectly to a roll for fully or partly irregular or regular distribution coating, contact application by means of a fixed gluing nip to a moving roll or product web, extrusion arrangement, e.g. hot gluing arrangements.

In accordance with this embodiment, it is possible to produce ply bonding solely by chemical means by gluing at least part of the contact surface area. Preferably, however, the plies to be bonded are exposed also to mechanical force, more particularly as exerted by embossing techniques. It is particularly preferred to apply the adhesive to the contact points produced by mechanical embossing. Suitable embossing methods include foot-to-foot, top-to-ground (nested), border and perforation embossing as well as the various known embossing methods permitting joining the material webs together by contact of protruding and/or recessed areas at the protruding points, the recessed points or their flanks.

A particular preferred embossing technique employs two subsequent embossing rolls whereof the first one provides at least one ply with a microembossing pattern and the second one the same ply with a design pattern. Preferably, only the protruding sections of the design pattern are glued and adhesively joined with the neighbouring ply. This technique makes the product less stiff and enhances bulk softness, primarily through the influence of the microembossments. Such a technique is for instance disclosed in EP 1 395 706 A.

The invention claimed is:

1. A tissue paper wherein one or both outer sides of the tissue paper comprise a pH indicator substance printed on a barrier layer, wherein the pH indicator substance is printed in register with a pattern of the barrier layer.

2. The tissue paper according to claim 1, wherein the pH indicator substance is present in an amount of $10^{-5}$ weight % to $10^{-1}$ weight % based on the paper dry-weight.

3. The tissue paper according to claim 1, wherein the pH indicator substance is selected from the group consisting of litmus, alizarin(red)S, methyl red, bromophenol red and chlorophenol red.

4. The tissue paper according to claim 1, wherein the tissue paper is toilet paper.

5. A tissue paper, comprising:
one or more tissue plies;
a barrier layer provided on one or both outer sides of the paper; and
a pH indicator substance on an outer surface of the barrier layer, wherein the pH indicator substance is applied in register with a pattern of the barrier layer and further wherein the barrier layer is an impermeable film that prevents an interaction between the paper ply and the pH indicator substance.

6. The tissue paper according to claim 5, wherein the barrier layer is an impermeable film comprising polyolefin, polyester, polyamide, wax or a combination thereof.

7. The tissue paper according to claim 5, wherein a solid ink formulation comprising the pH indicator substance and a polymeric binder or wax is solidified on the outer surface of the barrier layer.

8. The tissue paper according to claim 5, wherein the pattern of the barrier layer has a width in a range of 1 to 3 mm, and the pH indicator substance in register with the pattern of the barrier layer has a width in a range of 0.5 to 2.5 mm.

9. The tissue paper according to claim 5, wherein the tissue paper is toilet paper.

* * * * *